United States Patent
Luttropp et al.

(10) Patent No.: US 9,902,939 B2
(45) Date of Patent: Feb. 27, 2018

(54) DEVICE FOR RENAL CELL EXPANSION

(75) Inventors: David Luttropp, Frankfurt (DE);
Markus Neubauer, Balingen (DE);
Helmut Geiger, Wehrheim (DE);
Juergen Bereiter-Hahn, Hofheim (DE); Patrick Baer, Darmstadt (DE);
Reinhold Deppisch, Hechingen (DE);
Doris Deppisch, Hechingen (DE)

(73) Assignee: Gambro Lundia AB, Lund (SE)

( * ) Notice: Subject to any disclaimer, the term of this patent is extended or adjusted under 35 U.S.C. 154(b) by 558 days.

(21) Appl. No.: 13/120,323

(22) PCT Filed: Sep. 23, 2009

(86) PCT No.: PCT/EP2009/006850
§ 371 (c)(1),
(2), (4) Date: Apr. 27, 2011

(87) PCT Pub. No.: WO2010/034469
PCT Pub. Date: Apr. 1, 2010

(65) Prior Publication Data
US 2012/0145626 A1    Jun. 14, 2012

(30) Foreign Application Priority Data
Sep. 25, 2008  (EP) .................................. 08016812

(51) Int. Cl.
*C12M 3/00* (2006.01)
*B01D 71/42* (2006.01)
(Continued)

(52) U.S. Cl.
CPC .......... *C12N 5/0686* (2013.01); *C12M 21/08* (2013.01); *C12M 25/10* (2013.01); *C12M 29/16* (2013.01);
(Continued)

(58) Field of Classification Search
CPC ........ A61M 1/16; A61M 1/3489; A61M 1/34; A61M 1/3673; A61M 1/3689;
(Continued)

(56) References Cited

U.S. PATENT DOCUMENTS

| 4,056,467 A | 11/1977 | Christen et al. |
| 4,749,619 A | 6/1988 | Angleraud |

(Continued)

FOREIGN PATENT DOCUMENTS

| EP | 0 362 588 A1 | 4/1990 |
| EP | 0 550 798 A1 | 7/1993 |

(Continued)

OTHER PUBLICATIONS

Jacques Chanard, Sylvie Lavaud, Bruno Paris, Fatouma Toure, Philippe Rieu, Jean-Louis Renaux, and Michel Thomas; Assessment of Heparin Binding to the AN69 ST Hemodialysis Membrane: I. Preclinical Studies; ASAIO Journal Jul./Aug. 2005—vol. 51—Issue 4—pp. 342-347.*

(Continued)

*Primary Examiner* — Pranav N Patel
(74) *Attorney, Agent, or Firm* — Barnes & Thornburg LLP (57) ABSTRACT

A device for culturing, storing and expanding adherent renal cells. The device permits the adhesion and proliferation of the cells and the surface characteristics of the membrane material used in said device further permit the cellular matrix components (EMC). A method for expanding adherent renal cells and methods of using particular membranes for culturing, storing and expanding adherent renal cells. The membranes comprise a copolymer of acrylonitrile and sodium methallyl sulfonate as well as polyethylenimine.

17 Claims, 7 Drawing Sheets

(51) Int. Cl.
  *C12N 5/071* (2010.01)
  *C12M 1/12* (2006.01)
  *C12M 1/00* (2006.01)
  *B01D 71/68* (2006.01)

(52) U.S. Cl.
  CPC .............. *B01D 71/42* (2013.01); *B01D 71/68* (2013.01); *C12N 2533/30* (2013.01)

(58) Field of Classification Search
  CPC ...... A61M 2202/09; A61M 2210/1071; A61M 2210/1082; C12N 2533/30; C12N 5/0686; C12N 2502/256; C12N 5/0068; C12N 5/0687; C12M 25/10; C12M 29/16; C12M 21/08; C12M 23/06; A61L 33/0011
  USPC ............ 210/500.37, 500.24, 500.27, 500.23, 210/500.43, 650, 490, 321.71, 321.79, 210/321.8, 321.88, 321.89, 321.7, 9; 435/289.1, 297.1, 297.4, 298.1, 400, 401, 435/402, 369
  See application file for complete search history.

(56) References Cited

U.S. PATENT DOCUMENTS

| | | |
|---|---|---|
| 4,935,141 A | 6/1990 | Buck et al. |
| 5,369,012 A | 11/1994 | Koontz et al. |
| 5,686,289 A | 11/1997 | Humes et al. |
| 5,891,338 A | 4/1999 | Bell et al. |
| 6,103,117 A | 8/2000 | Shimagaki et al. |
| 6,150,164 A | 11/2000 | Humes |
| 6,942,879 B2 | 9/2005 | Humes |
| 6,960,297 B2 | 11/2005 | Kozawa et al. |
| 7,470,368 B2 | 12/2008 | Sugaya et al. |
| 7,837,042 B2 | 11/2010 | Yokota et al. |
| 2003/0021826 A1 | 1/2003 | Crost et al. |
| 2003/0203478 A1 | 10/2003 | Cadwell |
| 2004/0062809 A1 | 4/2004 | Honiger et al. |
| 2005/0045554 A1* | 3/2005 | Moachon et al. ........ 210/500.23 |
| 2005/0238687 A1 | 10/2005 | Humes |
| 2006/0191844 A1 | 8/2006 | Mahuchi et al. |
| 2006/0234582 A1 | 10/2006 | Gohl et al. |
| 2007/0082393 A1 | 4/2007 | Lodhi et al. |
| 2007/0269489 A1 | 11/2007 | Humes |

FOREIGN PATENT DOCUMENTS

| | | |
|---|---|---|
| EP | 0 925 826 A1 | 6/1999 |
| EP | 0925826 | 6/1999 |
| EP | 1 439 212 A1 | 7/2004 |
| EP | 1 875 957 A1 | 7/2006 |
| EP | 1 795 254 A1 | 6/2007 |
| EP | 2 133 298 A1 | 4/2009 |
| EP | 2 113 298 A9 | 11/2009 |
| EP | 1 578 521 B1 | 8/2010 |
| JP | 2003-245526 A | 9/2003 |
| JP | 2004305840 A | 11/2004 |
| WO | 1989/01967 A1 | 3/1989 |
| WO | 1990/011820 A2 | 10/1990 |
| WO | 1993/00439 A1 | 1/1993 |
| WO | 2001/54802 A1 | 8/2001 |
| WO | 2001/56549 A1 | 8/2001 |
| WO | WO2001/54802 | 8/2001 |
| WO | 2002/00775 A1 | 1/2002 |
| WO | WO2002/00775 | 1/2002 |
| WO | 2004/056459 A1 | 7/2004 |
| WO | 2004/056460 A1 | 7/2004 |
| WO | 2005/021139 A1 | 3/2005 |
| WO | WO2005/021139 | 3/2005 |
| WO | 2006/135966 A1 | 12/2006 |
| WO | 2006/138537 A2 | 12/2006 |
| WO | 2007/148147 A1 | 12/2007 |
| WO | WO2007/148147 | 12/2007 |
| WO | 2008/046779 A1 | 4/2008 |
| WO | 2010/034466 A1 | 4/2010 |
| WO | 2010/034468 A1 | 4/2010 |
| WO | 2010/034469 A1 | 4/2010 |
| WO | 2010/034475 A1 | 4/2010 |
| WO | WO2010/034466 | 4/2010 |
| WO | WO2010/034468 | 4/2010 |
| WO | WO2010/034475 | 4/2010 |

OTHER PUBLICATIONS

Hans Peter Wendel, Gerhard Ziemer, Coating-techniques to improve the hemocompatibility of arti®cial devices used for extracorporeal circulation, European Journal of Cardio-thoracic Surgery 16 (1999) 342-350.*

Aebischer et al., "Renal Epithelial Cells Grown on Semipermeable Hollow Fibers as a Potential Ultrafiltrate Processor", vol. XXXiii Trans Am Soc Artif Intern Organs, 1987, pp. 96-102.

Aebischer et al., "The Bioartificial Kidney: Progress towards an Ultrafiltration Device with Renal Epithelial Cells processing", Life Support Systems (1987), 5, 159-168.

Andrade et al., "Surface Characterization of Poly(Hydroxyethyl Methacrylate) and Related Polymers. I. Contact Angle Methods in Water", Journal of Polymer Science: Polymer Symposium 66, 313-336 (1979).

Anthony Atala, "Recent developments in tissue engineering and regenerative medicine", Current Opinion in Pediatrics, 2008, 18:167-171.

Baer et al., "Isolation of proximal and distal tubule cells from human kidney by immunomagnetic separation", Kidney International, vol. 52 (1997), pp. 1321-1331.

Fey-Lamprecht et al., "Functionality of MDCK kidney tubular cells on flat polymer membranes for biohybrid kidney", Journal of Materials Science: Materials in Medicine 9 (1998) 711-715.

William H. Fissell, "Developments towards an artificial kidney", Future Drugs Ltd., 2006, 155-165.

Green et al., "Measurement of the Transmittance Coefficient Spectrum of Cuprophan and RP69 Membranes: Applications to Middle Molecule Removal via Ultrafiltration", vol. XXII Trans. Amer. Soc. Artif. Int. Organs, 1976, pp. 627-636.

Humes et al., "The bioartificial kidney in the treatment of acute renal failure", Kidney International, vol. 61, Supplement 80 (2002), pp. S121-S125.

Humes et al.,"Tissue engineering of a bioartificial renal tubule assist device: In vitro transport and metabolic characteristics", Kidney International, vol. 55 (1999), pp. 2502-2514.

Akira Saito, "Research into the development of a Wearable Bioartificial Kidney with a Continuous Hemofilter and a Bioartificial Tubule Device Using Tubular Epithelial Cells", Artificial Organs, 28(1):58-63, 2004.

Saito et al., "Present Status and Perspective of the Development of a Bioartificial Kidney for Chronic Renal Failure Patients", Therapeutic Apheresis and Dialysis, 10(4):342-347, 2006.

Sciarratta et al., "Plasma functionalization of polypropylene with acrylic acid", Surface and Coatings Technology 174-175—(2003) 805-810.

International search report from PCT/EP2009/006847 completed Nov. 24, 2009, 10 pages.

International search report from PCT/EP2009/006850 completed Jan. 5, 2010, 9 pages.

International search report from PCT/EP2009/006860 completed Dec. 4, 2009, 10 pages.

Humes et al., 1999, "Replacement of Renal Function in Uremic Animals with a Tissue-Engineered kidney", Nature Biotechnology, 17, 451-455.

International Search Report/Written Opinion for PCT/EP2009/006850, completed Jan. 5, 2010.

International search report for PCT/EP2009/006849, completed Nov. 2, 2009.

* cited by examiner

Figure 1

Figure 2 (Scale bar = 20 μm)

Figure 3 (Scale bar = 100 µm)

DEVICE FOR RENAL CELL EXPANSION

TECHNICAL FIELD

The invention relates to a device which can be used for culturing, storing and expanding adherent renal cells, wherein said device allows for the adhesion and proliferation of the cells and the surface characteristics of the membrane material used in said device further allow for the membrane to be used without any pre-treatment with extracellular matrix components (EMC). The invention further relates to a method for expanding adherent renal cells, and to methods of using particular membranes for culturing, storing and expanding adherent renal cells. The invention further relates to a culture medium for use in said device and methods.

BACKGROUND OF THE INVENTION

Like most cells in vivo, many cells are adherent cells, or anchorage-dependent cells; that is, they can metabolize and divide only if they are attached to a surface or substrate. Only cells of the circulatory system (e.g., lymphocytes and red blood cells) grow unattached and suspended in solution in vitro. While many anchorage-dependent cells may grow on glass or synthetic surfaces, these cells often lose their ability to differentiate and respond to hormones. The loss of cellular morphology not only entails a loss of function, but also prevents regenerative power in a longer-term culture system. Longer-term cultivation would however be of great significance, for example, with the use of human cells for tissue culture, and many cells are not available in any quantity. For this reason, such tissue culture dishes are often coated with extracellular matrix components such as collagen or fibronectin. However, the use of xenogenic factors is a clear disadvantage, especially if the cells as such or on a matrix as used for medical treatment of human beings, as it will bring along risks of contamination and may result in adverse reactions in the patient treated.

The failure of cells to grow on such surfaces or keep their abilities is a major limitation of current tissue culture techniques. Tissue cultures are a potential source of tissues and organs which could be used for transplantation into humans. For example, tissue cultured skin cells could potentially be used in skin grafts. The aim is to develop biological substitutes that can restore and maintain normal function, for example, by the use of acellular matrices, which will depend on the body's ability to regenerate for proper orientation and direction of new tissue growth, or by the use of matrices or membranes with cells adhered thereto (*Curr. Opin. Pediatr.* 16, 167-171). Cells can also be used for therapy via injection, either with carriers or alone. In such cases, the cells need to be expanded in culture, attached to a support matrix, and then re-implanted into the host after expansion.

The ability to culture cells, especially adherent cells, is important also because they represent biological "factories" capable of producing large quantities of bio products such as growth factors, antibodies and viruses. These products can then be isolated from the cell cultures and used, for example, to treat human diseases.

Cell cultures also are emerging tools for biocompatibility and toxicology studies in the field of pharmaceutical and life science industry.

Finally, tissue cultures usually comprise cells from only one or a few tissues or organs. Consequently, cell cultures provide scientists with a system for studying the properties of individual cell types without the complications of working with the entire organism.

A known method for adherent cell cultures involves a hollow fiber membrane bioreactor. In this system, the cells are generally attached to the lumen of a cylindrical hollow fiber membrane. Culture media and oxygen flows through the hollow fiber membrane. The molecular weight cut-off of the membrane permits nutrients and oxygen to reach the cells without allowing the cells to escape.

A variety of polymers has been suggested for producing semipermeable membranes for cell and tissue culture (US 2007/269489). They include polyalginate, polyvinylchloride, polyvinylidenefluoride, polyurethane, cellulose acetate, cellulose diacetate, cellulose triacetate, cellulose nitrate, polysulfone, polyethersulfone, polystyrene, polyurethane, polyvinyl alcohol, polyacrylonitrile, polyamide, polymethylmethacrylate, polytetrafluoroethylene, polyethylene oxide and combinations of such polymers. The polymeric support may also consist of polyethyleneterephthalate (PET) or polycarbonate. Further materials which were suggested, for example, as scaffolds for transplantable tissue material, are cellulose or macroporous collagen carriers, or biodegradable matrices.

Apart from the problem of identifying membranes which could be used as a matrix for the cultivation of adherent cells, membranes currently known in the art suffer from their inability to sufficiently promote and sustain adherence, expansion, differentiation and extended life-span without the pre-treatment of said membranes or matrices, or the addition of exogenous factors, such as, for example, fibronectin, laminin or collagen.

In *Expert Rev. Med. Devices* 3(2), 155, efforts are reviewed with regard to developing an artificial kidney based on adhering renal tubule cells to a synthetic polysulfone-based hollow-fiber membrane. In this case the membrane has to be coated with ProNectin-L™ in order to promote attachment of the cells.

U.S. Pat. Nos. 6,150,164 A and 6,942,879 B1 both present elaborate ways towards a bio-artificial kidney based on renal cells such as, for example, endothelial cells or so-called renal stem cells, which are seeded into hollow fibers. Hollow fiber membranes which are mentioned as being useful are based on cellulose, polyacrylonitrile, polysulfone and other components or copolymers thereof. The internal or external surface of the hollow fiber is pre-coated with suitable extracellular matrix components (EMC) including Type I collagen, Type IV collagen, laminin, Matrigel, proteoglycan, fibronectin and combinations thereof. Only after such treatment the cells can be seeded.

J. Mat. Sci. 9 (1998) 711 discloses the cultivation of cloned Madin Darby Canine Kidney (MDCK) renal epithelial cells on the surfaces of polysulfone and polyacrylonitrile membranes, respectively. The MDCK cells were able to form epithelial-like layers on the membranes.

WO 02/00775 A1 discloses cultivation of chondrocytes on foam supports made of a copolymer of acrylonitrile and sodium methallylsulfonate (AN69). It is proposed that the foams can also be used for the cultivation of stem cells, keratocytes, hepatocytes, and islets of Langerhans. No mention is made of renal cells.

SUMMARY OF THE INVENTION

The present invention provides methods of using membranes for the cultivation, expansion differentiation, manipulation (e.g. transfection), and storage of adherent renal cells, with high performance characteristics without having to pre-treat or pre-coat the membranes with any extracellular matrix components (EMC). The present invention also provides a device which can be used for culturing, storing, differentiating, manipulating (e.g. transfecting) and expanding adherent renal cells, wherein said device allows for the adhesion and proliferation of the cells and the surface characteristics of the membrane material used in said device make it possible to use the membrane without any pre-treatment with extracellular matrix components. The invention further relates to a culture medium for use in said device and methods.

BRIEF DESCRIPTION OF THE DRAWINGS

FIG. 1 shows a schematic cross-sectional view of a device which can be used for culturing, storing and expanding adherent cells. The device comprises a bundle of hollow fiber membranes (1) contained within an outer shell (2). The fiber bundle is supported at its ends by end walls (3) made of a potting material. The end walls (3) also form a seal between the intracapillary compartment of the fibers and the extracapillary compartment of the device. Inlets/outlets (4) provide access to the intracapillary compartment of the device, while inlets/outlets (5) provide access to the extra-capillary compartment of the device.

DETAILED DESCRIPTION OF THE INVENTION

In one aspect of the present invention, the membrane can be used for cell attachment or adherence and cell cultivation or expansion without having to pre-treat or pre-coat the membrane with EMC. Advantages of using a membrane for cell cultivation without any such EMC are, for example, lower cost in terms of time savings and less process steps, a significantly reduced risk of contamination brought along with the EMC (GMP-compliance) or the higher number of process steps needed for coating a membrane and significantly better defined materials and protocols for cell production.

In a further aspect of the present invention, the performance in expanding and culturing cells can be significantly improved by preparing a hollow fiber membrane according to the invention, and by using said hollow fiber membrane or hollow fiber membrane bundle in a continuous culture process as an alternative to plate culture techniques.

The membrane used in the invention can be prepared in a way that confers the specific adhesive properties to the whole of the membrane, i.e., in case of a hollow fiber membrane for continuous applications, to the outside and inside of the hollow fiber membrane.

It is, however, also possible to prepare the membrane with surfaces on the outside and the inside (lumen side) of the hollow fiber membrane which differ in their adhesive properties. In case the cells are cultivated only on the inside of the hollow fibers, hollow fiber membranes according to the invention can be prepared which present specific adhesive properties on the inside of the hollow fibers. It is equally possible to prepare hollow fiber membranes according to the invention which show specific adhesive properties on the outside. Accordingly, hollow fiber membranes can be prepared to be used in applications which require adhesion and cultivation of cells on the inside or the outside only.

A further aspect of the present invention is that the membrane promotes the formation of a cell monolayer which is optimal in terms of differentiation and integrity without the need to pre-coat the membrane surface with any EMC. According to the invention, the membrane provides for retention of typical cell morphology, a monolayer is readily formed and tight junctions can be created. In the context of the present invention, a monolayer refers to a layer of cells in which no cell is growing on top of another, but all are growing side by side and are often touching each other on the same growth surface, even though this is not necessary for all potential applications of the membrane.

The membrane according to the invention can thus be advantageously used, for example, (a) in tissue culture technology, i.e. for establishing bio-artificial implants, such as bio-artificial kidneys (see also Curr. Opin. Pediatr. 16, 167-171);

(b) for expanding and storing adherent renal cells for use in medical therapies via injection of cells, which need to be expanded in vitro before being reimplanted into the host, such as, for example, renal endothelial cells;

(c) for expanding and providing adherent renal cells which serve as producers of bio products such as growth factors, recombinant proteins, cytokines or antibodies, such as monoclonal antibodies;

(d) for preparing cultures of adherent renal cells, preferably cell monolayer cultures, for studying specific cell types or for studying the influence of any drugs on cells (screening procedures), such as, for example, anti-cancer agents, anti-fungal, antibiotic, anti-viral (including anti-HIV) and anti-parasitic drugs;

(e) or any other application which is based on or requires the culturing expansion or storage of renal adherent cells in an in vitro system.

The membrane according to the invention can have any suitable geometry according to the needs of the intended use, i.e. it can be used as a flat sheet, a hollow fiber or a bundle of hollow fibers, or can be shaped to form chambers or other geometries needed. The core unit for cell expansion preferably is a hollow fiber-based membrane system allowing sufficient exchange of $O_2$ and $CO_2$, supply of nutrients and removal of waste products. The surface of the membrane is designed to enable adhesion and proliferation of cells properties through specific surface characteristics. The advantages of the cultivation of cells inside of hollow fibers is based on the advantageous surface to volume ratio which results in the minimization of medium consumption in the cultivation process, the minimization of space requirement and minimization of labor as compared to conventional flask or cell stack culture methods.

The membrane used in the invention is prepared from a copolymer of acrylonitrile and sodium methallylsulfonate. The proportion of sodium methallylsulfonate in the copolymer ranges from 3 to 15 percent by weight. The copolymers usually have a specific viscosity (measured at 25° C. in a dimethylformamide solution containing 2 g/l) of from 0.1 to 3, preferably 0.5 to 1.5. In one embodiment, the copolymer comprises about 3.3 mol-% sulfonic acid groups or sulfonate groups, respectively, and has an average molecular weight of about 250,000 Da. The copolymer is sold by Hospal Industrie under the trade name AN69.

An illustrative manufacturing process comprises the steps of:
(a) preparing a solution comprising
  i) a copolymer of polyacrylonitrile and sodium methallylsulfonate,
  ii) at least one solvent for said copolymer,
  iii) optionally, at least one non-solvent for the copolymer;
(b) extruding this solution in order to form a hollow fiber or a flat membrane;
(c) simultaneously, in the case of the preparation of a hollow fiber membrane, or after extrusion in the case of the formation of a flat membrane, solidifying the membrane obtained by a phase inversion process by partial or total contact of the extruded product with a liquid or gaseous fluid which is chemically inert with respect to the said polymers;
(d) washing the flat membrane or the hollow fiber membrane obtained;
(e) optionally, treating the flat membrane or the hollow fiber membrane with glycerol.

For preparing a flat sheet membrane according to the invention, the polymer is dissolved in the solvent at constant conditions. Degassing of the polymer solution is done in a drying oven creating a vacuum (approximately 100 mbar). The temperature of the polymer solution may vary over a relatively broad range. It is advantageous to choose a temperature ranging from ambient temperature to up to 60° C.

Suitable solvents for the copolymer are dimethylsulfoxide (DMSO), N,N-dimethylacetamide, N-methylpyrrolid-2-one, gamma-butyrolactone and especially N,N-dimethylformamide (DMF).

The polymer solution is then cast as a uniform film onto a smooth surface such as a glass slide which acts as a supporting area, by utilizing a special coating knife. The velocity of casting the polymer film can vary over a relatively broad range. A velocity between 10 and 20 mm/s may be used. In an exemplary lab-scale procedure, the polymer solution is applied steady-going onto the glass slide using a syringe. It is important to work bubble-free. The coating knife with a defined gap height is driven with constant velocity, creating a uniform polymer film. For a good thickness distribution, a coating knife having a uniform gap is advisable.

The temperature of the polymer solution may vary. Temperatures from ambient temperature up to 60° C. can be used.

The precipitation bath preferably consists of $H_2O$ and optionally a solvent. The bath preferably comprises $H_2O$ in amount of from 30 wt.-% to 100 wt.-% and a solvent selected from N-methyl-2-pyrrolidone (NMP), N-ethyl-2-pyrrolidone (NEP), N-octyl-2-pyrrolildone (NOP), dimethylacetamide, dimethylformamide (DMF), dimethylsulfoxide (DMSO) or gamma-butyrolactone (GBL) and mixtures thereof in an amount of from 70 wt.-% to 0 wt.-%. In one embodiment of the process, the precipitation bath comprises $H_2O$ in an amount of from 56 to 66 wt.-%, and a solvent in an amount of from 34 to 44 wt.-%. DMF is an especially suitable solvent.

The precipitated membrane is then stored in a non-solvent until the membrane is cut. After cutting, the membranes usually are washed, dried and sterilized.

There are two ways for producing membranes according to the invention which may be referred to a "wet" and "dry". In case "wet" fibers are prepared, the membranes have to be dried separately in a tube or oven after they have been prepared. To this end, bundles of fibers (for example, from 30 to 200 fibers) are placed in a plastic or metal tube. Hot air is passed through this tube within the bundles to dry the fibers.

Hollow fiber membranes according to the invention can also be obtained by:
(a) forming a spinnable homogeneous solution containing a copolymer of acrylonitrile and sodium methallylsulfonate which may be salified and may comprise a polar organic solvent, and an adjuvant;
(b) spinning said solution through a spinneret at a temperature above its gelling point, to form a hollow fiber and cooling the hollow fiber thus formed until it gels, and
(c) washing the gelled hollow fiber to remove the non-polymeric residues therefrom.

The composition used in this process essentially contains:
(i) a copolymer of acrylonitrile and sodium methallylsulfonate;
(ii) a polar organic solvent for the copolymer, and
(iii) an adjuvant which is a poor solvent or non-solvent for the copolymer and which is miscible with the solvent and preferably miscible with water.

The solvent used in the composition to be spun is a polar organic solvent or a mixture of polar organic solvents which is capable of forming a spinnable solution with the copolymer. Known solvents for the copolymer, which are preferably miscible with water, are generally used as the polar organic solvents. More specifically, there may be mentioned dimethylsulfoxide (DMSO), N,N-dimethylacetamide, N-methylpyrrolid-2-one, gamma-butyrolactone and especially N,N-dimethylformamide (DMF). The solution can be obtained from a mixture of solvents instead of from a single solvent.

One or more components which are poor solvents or non-solvents for the copolymer and which are miscible with the solvent or mixture of solvents, and preferably miscible with water, are used as adjuvants. The adjuvant facilitates the formation of a thermally reversible gel which is obtained by lowering the temperature of a solution having the composition defined above. It does not contain any component capable of reacting with components of the composition which would lead to the formation of an irreversible gel.

Examples of adjuvants which can be used are ethylene glycol, hexanediol, diethylene glycol and its monoethers such as 2-ethoxyethanol and 2-butoxyethanol, and urea. However, it is preferred to use water and/or especially glycerol because they are non-toxic and convenient to use.

Advantageously, the concentration of glycerol in the composition is adjusted to a level sufficient for the gelling temperature of the composition to be slightly above 100° C., which enables the solutions spun into a gelled hollow fiber to be cooled simply in air at ambient temperature.

In practice, the adjuvants are employed in the composition in amounts such that the concentration by weight of the copolymer is generally more than 5% and less than 50%. It is preferably between 20% and 40% by weight. The ratio of solvent to adjuvant is generally from 100/1 to 0.1/1 by weight and is preferably from 10/1 to 1/1.

The temperature of the composition defined in this way is brought to values above the gelling temperature, which is generally from 50° C. to 150° C., and preferably from 90° C. to 130° C.

The various constituents listed above are mixed and the mixture is heated to form a spinnable homogeneous solution. The process can be carried out in a manner known to the person skilled in the art, in any suitable apparatus equipped with heating and stirring means, such as a dissolver or, preferably, an extruder.

The solution prepared in this way can be spun in the form of hollow fibers by various processes which are known to the person skilled in the art. The spinneret is generally of annular shape. It is preferably arranged along a vertical axis. It also possesses an axial orifice allowing air or inert gas, which is advantageously filtered, to be introduced through the spinneret, thus contributing to the support and uniform shaping of the axial channel of the hollow fiber during formation.

The air or the gas can be introduced at ambient temperature and at a pressure of the order of atmospheric pressure or, advantageously, at a slight overpressure, for example at a relative pressure of less than 500 mm of water.

The semipermeable hollow fibers are essentially obtained by spinning the solution described above at constant rate, most frequently with the aid of an injection pump operating under pressure, and then cooling the spun solution below its gelling point.

The solution is thus converted from the liquid state to the gel state, that is to say to a non-fluid state still impregnated with solvent. In fact, all the components of the initial solution are retained in the gel. Slight losses of solvent or non-solvent by evaporation may possibly be observed, but these losses are generally not disadvantageous.

The essential factor in the conversion of this solution is the lowering of its temperature, which results in a gradual increase in its viscosity and also in the appearance of elastic properties, and which leads to a non-fluid uniform mass capable of retaining its shape under its own weight. This conversion could be reversed, if necessary.

The cooling can preferably be obtained simply by contact with the atmosphere, or by the forced circulation of air, cooled beforehand if appropriate, or by the action of any other fluid—liquid or gaseous—which is inert and immiscible with the constituents of the solution during gelling.

In one embodiment, the solution flows vertically from the spinneret during the gelling process. It is not until the hollow fiber has reached a sufficient state of solidification, enabling it to be subjected to mechanical stress while retaining its shape, that it is generally taken over by a mechanical system comprising, in particular, one or more drive rollers. In practice, the distance, and preferably the height, between the spinneret and the first mechanical element coming into contact with the hollow fiber after gelling is generally between 1 cm and 10 meters and preferably between 50 cm and 3 meters.

Advantageously, the hollow fiber is wound around a first drive roller, which is caused to rotate at a constant speed such that it exerts a so-called primary longitudinal stretching on the hollow fiber as soon as it leaves the spinneret, when the composition is still in the fluid state.

It is observed that this primary stretching results in a simultaneous reduction in the internal and especially external diameters of the hollow fiber, and hence in a substantial reduction in its thickness. It is thus possible to obtain fine hollow fibers using spinnerets having one or more relatively wide, annular orifices, which simplifies their construction and improves the uniformity of their operation. Moreover, the production rate of the hollow fiber can be increased considerably. The primary stretching ratio is in fact generally from 1/1 to 20/1 and preferably from 2/1 to 10/1.

This reduction in the thickness of the wall of the hollow fiber assists rapid cooling of the composition. This conversion leads to a homogeneous microporous structure without a skin, the pores still being impregnated with the solvent and adjuvant components. They are then removed by washing.

The microporous structure obtained according to the present invention is formed, in the gel state, of a mass which has on the whole retained all the constituents of the initial solution, in contrast to the processes involving either evaporation of the solvent or extraction of the solvent from a polymer solution by a coagulating agent (a non-solvent for the polymer, miscible with the solvent). The use of a coagulant is therefore advantageously avoided.

The non-polymeric residues, in particular the solvent and the adjuvant, are removed by washing the hollow fiber while it is in the gel state, that is to say non-fluid, by immersing it in a washing bath. It will be noted that this bath could only have a coagulating effect insofar as the hollow fiber was still in the fluid state and not yet converted to gel.

This washing can be carried out in one or more steps including a second treatment by so-called "secondary" stretching. The washing bath used can be an aqueous mixture of organic solvents, in particular of alcohols such as methanol, but it is preferred to use pure water. Generally, the temperature of the washing bath or baths is from 0° C. to 100° C. and preferably from 10° C. to 50° C. The residence time of the hollow fiber in the washing bath or baths is generally from 5 seconds to 5 minutes, and preferably from 30 seconds to 2 minutes.

The washing treatment before secondary stretching generally has the effect of increasing the rigidity of the hollow fiber and of reducing its permeability somewhat, which shows that there is no substantial coagulation process.

Advantageously, the porosity of the hollow fibers is increased and their permeability is thus adjusted in the desired range, depending on the application envisaged, by subjecting them to a further, so-called secondary, longitudinal stretching. This stretching is carried out when the hollow fiber is immersed in an aqueous medium, for example water or a water/solvent mixture. The temperature of the stretching bath is generally from 50° C. to 100° C. and preferably from 80° C. to 100° C. The secondary stretching ratio is generally from 1/1 to 10/1 and preferably from 1.5/1 to 6/1.

In an alternative process for the preparation of hollow fibers, a "collodion", formed from a solution of the copolymer in a polar organic solvent (or mixture of solvents) is injected into a spinneret with an annular orifice, and that, immediately at the outlet of the spinneret, the inside and the outside of the nascent hollow fiber are coagulated by means of a coagulating fluid which is either:

a) an aqueous solution of an inorganic salt of concentrations less than that required for saturation, usually between 1 and 35% by weight, and preferably between 5 and 20%, or b) a polar organic solvent or a mixture of polar organic solvents, this solvent (or mixture of solvents) being a non-solvent for the copolymer and being miscible with the solvent for the collodion.

By "collodion" is meant a spinnable solution of the copolymer. Known solvents for the copolymers are generally used as the polar organic solvent which is capable of forming the collodion, in particular dimethylsulfoxide, dimethylacetamide, hexamethylphosphorotriamide (HMPTA) and, especially, N,N-dimethylformamide (DMF). Instead of a single solvent, the collodion can be produced from a mixture of solvents; it is also possible to add a minor amount of a non-solvent for the polymer to this solvent or mixture of solvents, insofar as the whole remains a solvent for the copolymer.

The concentration of copolymer in the collodion is generally greater than 5% by weight and less than that required for saturation; it is preferably greater than 20% by weight.

The collodion is then coagulated by simply bringing the collodion into contact with the coagulating fluid, immediately at the outlet of the spinneret. The difference in temperature between the collodion and the coagulating fluid is generally less than 30° C.

The external coagulation of the nascent hollow fiber is effected in practice by making the fiber, during its formation, to flow through a bath of coagulating fluid ("coagulating bath").

The internal coagulation of the nascent hollow fiber is effected in practice by injecting coagulating fluid into the core, that is to say into the inside of the fiber during its formation.

The temperature of the coagulating fluids and of the collodion can vary within wide limits; they are generally between −10 and +40° C., and preferably between 0 and 30° C. Low temperatures generally favor the absence of vacuoles. The temperatures of the collodion, of the internal coagulating fluid and of the spinneret are usually the same for economic and technical reasons; in contrast, the temperature of the coagulating bath can be different from the other three.

When the coagulating fluid is an aqueous solution of an inorganic salt, a salt of an alkali metal or alkaline earth metal which is soluble in water is advantageously used; it is generally preferred to use sodium chloride. It is however also possible to use lithium, sodium, potassium, magnesium and calcium chlorides, sulfates, nitrates and perchlorates, within the limits of their solubility.

The non-solvent power of these aqueous solutions can be altered by adding miscible polar organic solvents, for example dimethylformamide, in a proportion which is preferably less than 40% (by volume).

When the coagulating fluid is a polar organic solvent or a mixture of polar organic solvents, alcohols such as methanol, ethanol, propanols and butanols, aliphatic diols, especially ethylene glycol, or aliphatic ketones such as acetone and methyl ethyl ketone, are advantageously used as the non-solvent for the copolymer; the non-solvent power of this solvent or mixture of solvents can be changed by adding minor amounts (generally less than 25%) of solvents for the copolymer such as those mentioned above e.g. dimethylformamide, dimethylsulfoxide, dimethylacetamide and hexamethylphosphorotriamide.

During the coagulation, a part of the solvent for the collodion migrates into the coagulating fluid and this, consequently, can change the composition thereof somewhat.

For the purpose of ensuring that the hollow fibers have a uniform and symmetrical shape, it is preferred to position the spinneret along a vertical axis with the collodion flowing in a downwards direction; in practice, the spinnerets are immersed spinnerets.

The nascent fiber is kept in contact with the coagulating fluids at least until the fiber is sufficiently hardened to enable it to be handled and no longer flows under the working conditions.

The coagulation described above can be followed by washing with pure water in order to remove non-polymeric constituents from the fiber (especially solvents and/or salts).

The fibers, prepared by the coagulation process described above, can be given an aqueous heat treatment for the purposes of improving their performance, especially their permeability.

The hollow fibers subjected to this treatment can have undergone a partial washing with pure water or with a mixture of water and an organic solvent but, regardless of this, at the time of the aqueous heat treatment, the fibers still advantageously contain a little of the solvent or solvents which initially formed the collodion; more precisely, the proportion of residual solvent in the hollow fibers during the aqueous heat treatment is generally between 5 and 20%, and preferably between 10 and 17%.

This aqueous heat treatment generally consists of immersing the hollow fibers in water or in a mixture of water and a non-solvent at a temperature between 60° C. and 250° C., and preferably between 80° C. and 190° C.

The water or the aqueous mixtures used can be in the vapor phase; however, it is preferable to use them in the liquid phase. Of course, a treatment above 100° C. can make it necessary to work under pressure when it is desired to use liquid water in order to carry out the aqueous heat treatment.

The proportion of water in the aqueous mixtures which can be used in this treatment is usually greater than 50% by weight, and preferably greater than 90%. The water can be mixed with organic solvents or with inorganic or organic electrolytes but it is then preferred to use mixtures which are chemically neutral and especially not strongly basic so as to avoid chemical attack of the acrylonitrile copolymer. A pH of 6 to 8 is generally suitable.

According to an advantageous procedure, the aqueous heat treatment is carried out continuously by making the fiber flow continuously through the hot water treatment bath, the pressure being atmospheric and the temperature being at most equal to 100° C. The duration of the treatment is usually 5 seconds to 5 minutes but there is no critical upper limit.

The aqueous heat treatment described above is preferably accompanied by stretching the fibers longitudinally; this stretching is usually 50 to 500%, and preferably 100 to 250%.

To provide the fibers with a good dimensional stability on storage, it is advantageous to subject them to a relaxation treatment. To do this, they are passed through one or more baths of water, the temperature of which is above the use and/or storage temperature of the fiber. Generally, the temperature of the bath or baths is from 40° C. to 100° C. and preferably from 80° C. to 100° C. The hollow fiber is generally guided between the inlet and outlet of the bath by rollers, the relative speeds of which are adjusted so that the fiber is constantly kept immersed and slack.

This relaxation bath also makes it possible to carry out an additional washing of the hollow fiber and to remove the traces of non-polymeric residues. The residence time of the hollow fiber in the relaxation and/or washing bath is generally less than one minute.

The hollow fibers can be stored in an aseptic medium, for example in aqueous formaldehyde solution. They can also be impregnated with a water-retention agent, such as ethylene glycol or, preferably, glycerol, for example by immersion into a mixture of water and glycerol containing at least 40% by weight of glycerol, by techniques which are known in the art.

Other operating conditions for preparing the semipermeable membrane may be found in U.S. Pat. No. 4,749,619 (gelation process) or in U.S. Pat. No. 4,056,467 (coagulation process), both of which are incorporated herein by reference.

The selectively permeable hollow fibers are of the symmetrical type and have a homogeneous microporous structure, which is substantially uniform throughout their thickness. The average diameter of the micropores is generally less than 100 Å, this average diameter being determined by the method of D. M. Green et al., described in *Trans. Amer. Soc. Artif. Int. Organs,* 1976, 627ff. Moreover, the void factor is most frequently from 40% to 85% and preferably from 60% to 80%. The hollow fibers are generally free of vacuoles (empty spaces included in the wall and having a largest dimension of more than about 5 microns). They do not possess a skin or a dense layer on the surface, either on the inside or on the outside.

In one embodiment, the membrane is coated on one or both faces with polyethyleneimine (PEI). The PEI has an average molecular weight in excess of 25,000 Da, preferably more than 100,000 Da. In one embodiment, a polyethyleneimine having an average molecular weight of 750,000 Da (Lupasol® P, BASF Aktiengesellschaft) is used. In a further embodiment, the PEI is fractionated by ultrafiltration to remove low molecular weight fractions, before it is used for coating the membrane. Details of the ultrafiltration process are disclosed in US 2003/0021826 and WO 01/54802, both incorporated herein by reference. The amount of PEI coated on the membrane ranges from 1 to 80 mg/m$^2$ per face of the membrane.

The PEI can be combined with the membrane after the extrusion step for obtaining a hollow fiber or a flat membrane, according to a process comprising the steps of:
(a) preparing a flat membrane or a hollow fiber membrane, which has optionally been treated with glycerol, by a conventional process from a solution of a copolymer of polyacrylonitrile and sodium methallylsulfonate;
(b) simultaneously or successively, optionally removing the glycerol from the membrane and preparing a solution containing the PEI in dissolved form and bringing this solution into contact with the surface of the membrane;
(c) optionally, rinsing the membrane in order to remove the excess of non-bound PEI and, optionally, retreating the membrane with glycerol;
(d) sterilizing the membrane.

In the case of a flat semipermeable membrane, this membrane can be combined with PEI using a spraying process comprising the following steps:
(a) preparing a flat membrane, which has optionally been treated with glycerol, from a solution of a copolymer of polyacrylonitrile and sodium methallylsulfonate;
(b) simultaneously or consecutively, optionally removing the glycerol from the semipermeable membrane and preparing a solution containing the PEI in dissolved form and spraying this solution onto the surface of the membrane;
(c) optionally, rinsing the membrane in order to remove the excess of non-bound cationic polymer and, optionally, retreating the membrane with glycerol;
(d) sterilizing the membrane.

Further details of the process are disclosed in EP 0 925 826 A1, incorporated herein by reference. In one embodiment of the process, the membrane is sprayed with a 0.15 M NaCl solution comprising 40 mg/l PEI.

In the case of hollow fiber membranes, the solution containing the PEI is circulated through the lumen of the fibers to obtain a fiber coated on the inner surface of the fibers. To obtain fibers coated on the outer surface of the fibers, the PEI solution is circulated around the outside of the fibers. If both processes are combined, fibers coated both on the inner and the outer surfaces are prepared. Further details of the respective processes are disclosed in WO 01/54802 and WO 2005/021139, both incorporated herein by reference. Hollow fiber membranes having the surface of their lumen coated with PEI are also designated AN69ST and sold by Hospal Industrie under the trade name Nephral® ST The concentration of PEI in the solution ranges from 0.04 g/l to 30 g/l. The solvent can be water, mixtures of water and glycerol, salt buffers or salt solutions. The pH of the solutions ranges from 5 to 12. Treatment flow rates (in the case of circulating the solution through or around the fibers in a conventional dialyser setup) of 50 to 500 ml/min are generally suitable. The time required for the treatment generally is in the range of from 1 to 30 minutes. In one embodiment (disclosed in WO 2007/148147, incorporated herein by reference), the PEI solution contains PEI and citric acid in a weight ration of 0.7 to 1.3, e.g. 0.9 to 1.1, or even 1.0. A colloidal suspension of PEI in an acidic medium is formed, which allows to considerably increase both the quantity of PEI grafted to the surface of the copolymer membrane as well as the availability of free cationic or cationizable groups at the surface.

In addition to the coating with PEI, the membranes optionally are coated with heparin (fractionated or non-fractionated). In one embodiment of the coating process, the heparin concentration ranges from 1 to 200 IU/ml, for example 10 to 100 IU/ml; the medium is water, glycerinated water, a saline buffer, or a saline solution; the pH ranges from 3 to 10, e.g. 3 to 7, or 5 to 10; treatment flow rates (in the case of treating the membrane by circulation in a conventional ultrafiltration or dialyser device comprising the membranes) are from 50 to 500 ml/min; treatment duration is from 1 to 30 minutes; the process can be performed in open circuit or closed circuit. Under these conditions, the surface heparin concentration is between 200 and 20,000 IU/m$^2$, for instance between 500 and 10,000 IU/m$^2$. Further details of suitable processes are disclosed in WO 01/54802, US 2003/0021826, and WO 2007/148147, all incorporated herein by reference.

Depending on the case, the sterilization technique which will be used has to be without any significant effect on the bonding between the PEI and the semipermeable membrane, and may be sterilization by irradiation, in particular by gamma irradiation, or sterilization with ethylene oxide.

In a specific embodiment of the present invention, the membrane is a hollow fiber membrane. A hollow fiber membrane according to the invention is further characterized by having an inner diameter of between 50 and 2,000 μm, preferably of between 50 and 1,000 μm, and more preferably between 100 and 500 μm. The wall thickness is generally from 3% to 30% of the external diameter, that is to say generally from 5 to 200 μm and preferably from 10 to 80 μm, and more preferably from 25 to 50 μm.

In another specific embodiment of the present invention, the membrane is a flat sheet membrane. The thickness of a flat sheet membrane according to the invention may vary between 20 μm and 200 μm. A thickness of 35 μm to 50 μm may be especially advantageous for most applications. Usually, several flat sheet membranes will be combined in the form of a stack to form a module for use in the present invention.

The membrane according to the invention is a hydrophilic, semipermeable membrane. "Hydrophilic" membranes can be defined, in accordance with the present invention, by their ability to be spontaneously water-wettable without wetting aids. A membrane, independent of its shape, is called readily or spontaneously water-wettable if it is wetted by water virtually spotlessly. A semipermeable membrane allows nutrients and metabolizing gasses to pass from the cell-culture medium through the wall of the hollow fiber membrane to the cells, and cell waste products to pass from the cells to the medium on the other side of the membrane, while retaining cells and, as the case may be, larger secreted products.

The hydraulic permeability of a membrane according to the invention may vary from $1 \cdot 10^{-4}$ to $100 \cdot 10^{-4}$ cm$^3$/(cm$^2 \cdot$bar$\cdot$sec). In order to achieve such hydraulic permeability without getting defects in the membrane structure, the viscosity of the polymer solution should be in a range between 3,500 centipoise (cP) and 200,000 cP, preferably between 10,900 cP and 25,600 cP for hollow fiber production. For flat sheet membrane production the viscosity should be between 3,500 cP and 500,000 cP, preferably between 4,500 cP and 415,000 cP.

The selective cut-off of a membrane for cell culture is essential for keeping essential substances in the lumen by size exclusion. This is also of importance with regard to minimizing medium consumption in cases when growth medium is to be used only in the intracapillary (IC) side and not on the extracapillary side (EC) of hollow fiber membranes. In this case crucial components of fetal bovine serum (FBS) or platelet lysate-based media can be retained on the IC side and not diffuse from IC to EC and are no more available for cells located on the IC side. Preferably, the cutoff, defined by the average molecular weight of the molecules having a sieving coefficient of 0.1 in aqueous solution, of a membrane according to the present invention is between 10,000 and 100,000 Da.

The membrane according to the present invention can be advantageously used for culturing, expanding or storing adherent renal cells. Examples for such cells are renal epithelial cell lines MDCK (ATCC#CCL-34) or HK-2 (CRL#2190). In one embodiment of the invention, the membrane according to the invention will be used for culturing, expanding or storing renal endothelial cells, in particular human renal tubule cells. In one embodiment, the cells are primary human renal tubule cells e.g. human proximal tubule cells (hPTC) or human distal tubule cells (hDTC).

In one embodiment of the present invention, a membrane comprising a copolymer of acrylonitrile and sodium methallylsulfonate as described above, without any additional coating (e.g., AN69), is used for culturing adherent renal cells. This has proven to be effective in particular for renal epithelial cell lines MDCK and HK-2.

In another embodiment of the present invention, a membrane comprising a copolymer of acrylonitrile and sodium methallylsulfonate and further comprising polyethyleneimine as described above (e.g., AN69ST), is used for culturing adherent renal cells. It has been found that for primary human renal tubule cells, formation of confluent monolayers and cellular differentiation are improved in comparison with uncoated membranes.

In another embodiment of the present invention, a membrane further comprising heparin as described above, is used for culturing adherent renal cells. It has been found that proliferation of cells on the membrane is positively affected by the presence of heparin.

The membrane according to the invention can be used in various kinds of cell expansion or cell culturing devices or systems, such as described, for example, in WO 2005/021139, US 2003/0203478 A1, U.S. Pat. Nos. 6,150,164 or 6,942,879, all incorporated herein by reference.

Thus, a further aspect of the present invention is a device for culturing, storing and expanding adherent renal cells, comprising a membrane comprising a copolymer of acrylonitrile and sodium methallylsulfonate as described above. In one embodiment, the membrane further comprises polyethyleneimine. In another embodiment, the membrane further comprises heparin. Suitable membranes, their characteristics and processes for their production have been described above.

The membrane used in the device can take the form of a sheet or a plurality of sheets, e.g. a stack of planar membranes. Alternatively, the membrane used in the device can take the form of a hollow fiber or a plurality of hollow fibers, e.g. a bundle of hollow fiber membranes. Suitable sheets and fibers, respectively, their properties and preparation have been described above.

In one embodiment of the device, the membrane forms an interface between two fluid compartments of the device.

An exemplary device comprises two compartments separated by a semipermeable membrane mounted in a casing, a first internal compartment fitted with two accesses and a second external compartment comprising one or two accesses, both compartments being also separated by a potting compound, based on an appropriate adhesive compound, intended for forming as applicable (i) a cylindrical partition separating both compartments of said device containing a semipermeable membrane of the hollow fiber bundle type as defined above or (ii) a tight seal in said device including a semipermeable membrane of the sheet membrane type as defined above.

Another exemplary device comprises a plurality of hollow fiber membranes, contained within an outer shell, and configured so that fluid within a space external to the hollow fibers (i.e., an extracapillary compartment) is segregated from fluid passing through the hollow fibers and their corresponding orifices. Additionally, the device includes two manifold end chambers within the outer shell on opposite ends of the device. Each of the two orifices of a hollow fiber connects to a different end chamber. The end chambers and the extracapillary compartment are separated by the semipermeable membranes of the hollow fibers. The composition within the extracapillary compartment can be controlled, to a certain extent, by the molecular weight cutoff, or pore size, of the membranes of the hollow fibers.

In one mode of operating the device, cells are grown in the extracapillary compartment while a nutrient medium is passed through the hollow fibers. In another mode of operating the device, cells are grown in the intracapillary space (i.e. lumen) of the hollow fibers while a nutrient medium is passed through the extracapillary compartment and/or the intracapillary compartment. The semipermeable nature of the hollow fibers allows nutrients and cell waste products to pass through the walls of the hollow fibers while blocking cells from doing the same.

Shell-and-tube type bioreactors provide several advantages. For adherent cells, the use of several hollow fibers provides, within a relatively small volume, a large amount of surface area upon which the cells can grow. This large amount of surface area also facilitates localized distribution of nutrient media to the growing cells and ready collection of cell waste products. Shell-and-tube type bioreactors enable the growth of cells at much higher density rates than is possible with other cell culture devices. They can support cell densities greater than $10^8$ cells per milliliter, whereas other cell culture devices are typically limited to densities around $10^6$ cells per milliliter.

Another aspect of the present invention concerns a process for expanding adherent renal cells. In this process, the cells are cultured on a surface of a membrane comprising a copolymer of acrylonitrile and sodium methallylsulfonate as described above. In one embodiment, the membrane further comprises polyethyleneimine. In a further embodiment, the membrane also comprises heparin. Suitable membranes, their characteristics and processes for their production have been described above.

In one embodiment of the process, the adherent renal cells are cultured on the inner surface of a hollow fiber membrane comprising a copolymer of acrylonitrile and sodium methallylsulfonate. In another embodiment, the membrane further comprises polyethyleneimine. In a further embodiment, the membrane also comprises heparin. Suitable membranes, their characteristics and processes for their production have been described above.

In one embodiment of the process, the culturing comprises the steps of:

a) seeding the membrane with adherent renal cells;
b) propagating the adherent renal cells;
c) detaching the adherent renal cells from the membrane; and
d) collecting the detached adherent renal cells.

In one embodiment of the process, the adherent renal cells are renal epithelial cell lines MDCK (ATCC#CCL-34). In another embodiment of the process, the adherent renal cells are renal epithelial cell lines HK-2 (CRL#2190). In still another embodiment of the process, the adherent renal cells are primary human renal cells, in particular primary human renal tubule cells. In a further embodiment, the cells are human proximal tubule cells (hPTC). In still another embodiment, the cells are human distal tubule cells (hDTC).

In a first step of the process, the membrane is seeded with adherent renal cells. In one embodiment, a suspension of cells in PBS is used for seeding. A suitable concentration of suspended cells is in the range from $0.5 \cdot 10^6$ to $1.0 \cdot 10^6$ cells/ml.

Figure 1:
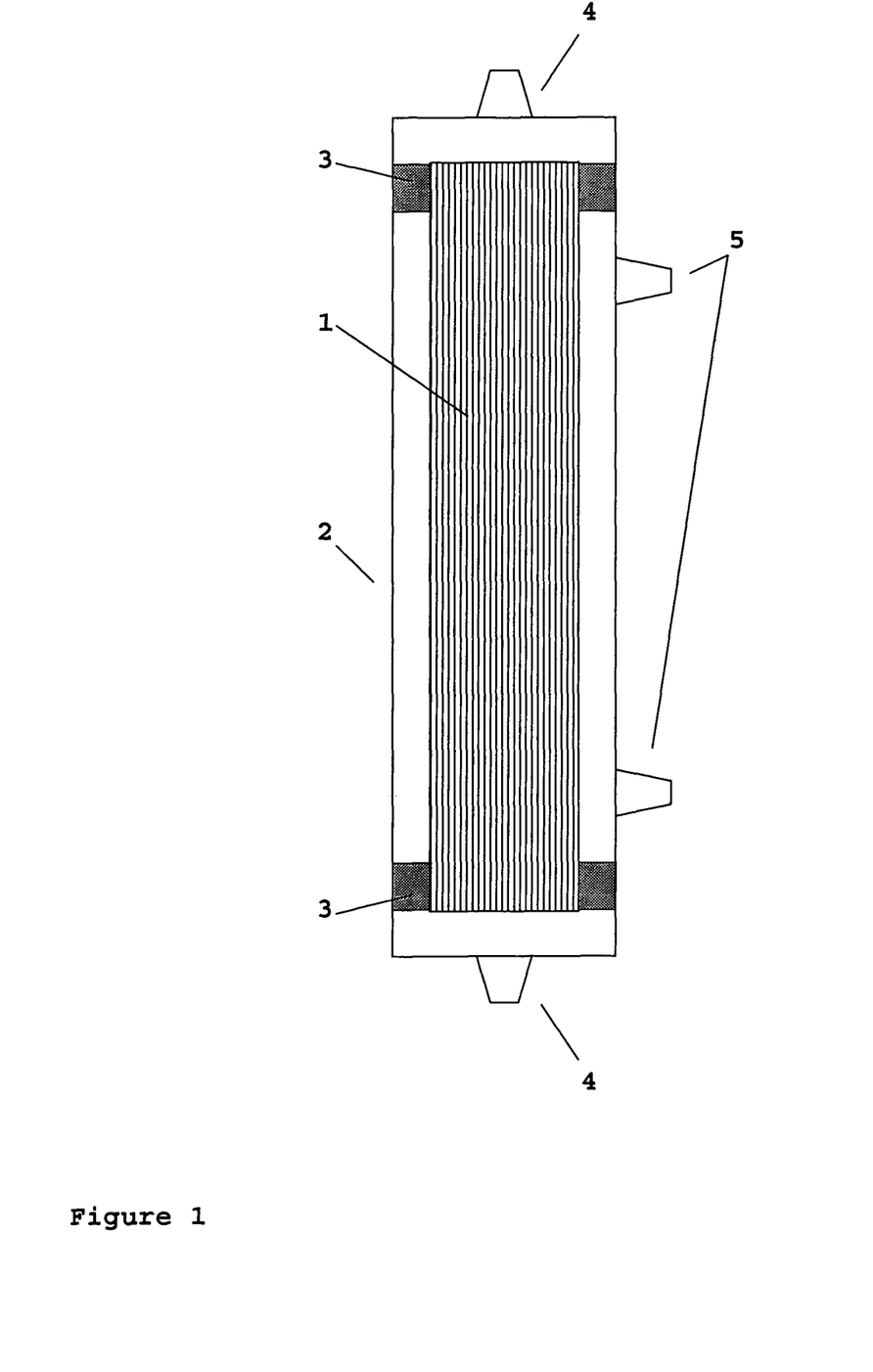

In case the process is performed in a device comprising a plurality of hollow fiber membranes (1), contained within an outer shell (2), as shown in FIG. 1, and the cells are to be cultured on the inner surface of the hollow fiber membranes, the fluid comprising the suspended seed cells can either be injected into the lumen of the hollow fibers through one of the inlets/outlets (4) of the intracapillary compartment, or circulated through the hollow fibers by means of a pump connected to the inlets/outlets (4) of the intracapillary compartment. In a particular embodiment, the device is simultaneously operated in filtration mode, i.e. fluid is withdrawn from the extracapillary compartment of the device through one of the inlets/outlets (5) of the extracapillary compartment during supply of the seed cell suspension to the lumen of the hollow fibers. Preferably, calcium-free suspension media are used. It has been found that the tendency of thrombus formation can be reduced thereby. Viability of the cells is improved, when in the preparation of the cell suspension accutase is used for cell separation instead of trypsin, and the temperature of the suspension is kept at 4° C. during the process. To improve uniform distribution of the cells, the device can be shaken or tilted periodically during the seeding process.

After the membrane has been seeded with adherent renal cells, the cells are propagated by culturing them under appropriate conditions using suitable culture media known in the art.

In one embodiment of the process which uses a device as shown in FIG. 1, the culture medium is circulated in the extracapillary compartment of the device to supply the cells in the hollow fiber membranes with nutrients and oxygen and to remove metabolites. In another embodiment of the process, culture medium is additionally circulated through the lumen of the hollow fiber membranes.

After completion of step b) of the process, the proliferated cells can be harvested. In one embodiment of the process, step b) is terminated after a confluent layer of adherent renal cells has been formed on the membrane. The adherent renal cells are detached from the membrane using a suitable enzyme, e.g. trypsin or accutase.

In one embodiment of the process using hollow fiber membranes, the hollow fibers are flushed with a solution comprising the enzyme to detach and remove the renal cells adhering to the inner surface of the hollow fibers.

The detached cells are collected and may be processed for further use. A fraction of the harvested cells can be used to initiate a further cycle of the process of the invention, e.g. as seed cells in step a) of the process.

It is a particular advantage of the process of the present invention for expanding adherent renal cells that the membrane can be reused in the process, optionally after a suitable cleaning step. A plurality of proliferation cycles can be performed using one and the same membrane, allowing for a quasi-continuous operation of the process. Thus, in one embodiment of the process, steps a) through d) are reiterated using one and the same membrane.

A further aspect of the invention is a culture medium for use in a device for culturing, storing and expanding adherent renal cells or a process for expanding adherent renal cells, respectively. The culture medium consists of a serum free and animal by-products free basal medium capable of supporting the growth of mammalian epithelial cells in vitro, 20 to 30 µg/ml BPE (Bovine Pituitary Extract), 1 to 20 ng/ml, e. g. 5 ng/ml EGF (Epidermal Growth Factor), 0.5 to 2 mmol/l, e.g. 1.2 mmol/l $Ca^{2+}$, and 0.5 to 3 vol.-%, e.g. 1 vol.-% FCS (Fetal Calf Serum). According to one embodiment, the culture medium consists of a serum free and animal byproducts free basal medium capable of supporting the growth of mammalian epithelial cells in vitro, 20 to 30 µg/ml BPE, 5 ng/ml EGF, 1.2 mmol/l $Ca^{2+}$, and 1 vol.-% FCS (Fetal Calf Serum). It has been found that the culture medium of the present invention improves both the number of cells as well as the cell density of the cultured cells. Additionally, the culture medium of the invention improves cell differentiation of cells grown on membranes according to the invention. The culture medium thus can be beneficially used in step b) of the process for expanding adherent renal cells according to the present invention.

A further aspect of the present invention concerns the use of a membrane comprising a copolymer of acrylonitrile and sodium methallylsulfonate, optionally polyethyleneimine, and optionally heparin, having renal cells adhered to the surface of the membrane, in an artificial kidney. It is envisioned that the renal cells adhered to the membrane perform some of the tasks of the cells in the kidney, e.g. the cells in the nephron, in particular the proximal or distal tubule. These tasks include homeostasis; excretion of metabolites like urea, uric acid, creatinine, toxines etc. from the blood; and resorption of aminoacids, proteins, peptide hormones, glucose etc. from the blood.

EXAMPLES

Example 1

Circular specimens having a diameter of 44 mm of A) a blend of polyamide, polyarylethersulfone and polyvinylpyrrolidon (Polyflux®, Gambro) and B) a copolymer of acrylonitrile and sodium methallylsufonate (AN69, Gambro) were cut from sheet membranes, placed in 60 mm petri dishes and secured with aluminum rings having a diameter of 38 mm. MDCK cells were seeded over the whole area of the petri dishes and cultured using M199 medium+10% FCS.

Figure 2:
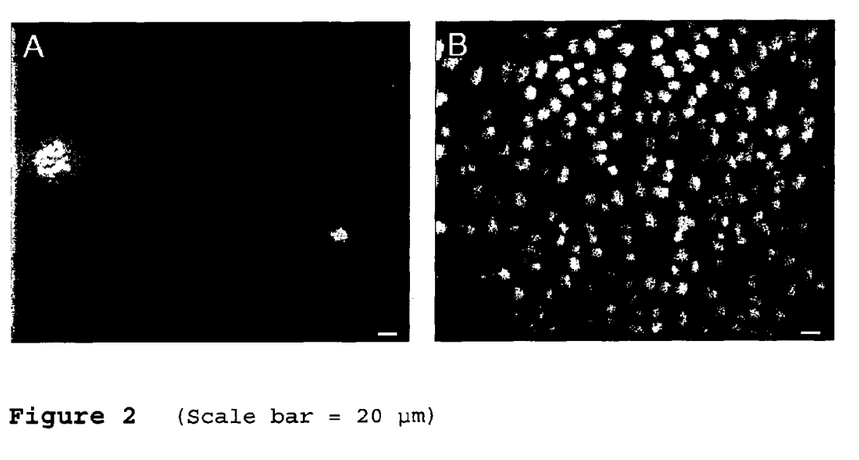
FIG. 2 shows LM micrographs of MDCK cells cultured for 24 hours on Polyflux® and AN69 membranes, respectively.

After 24 hours of culturing, almost no growth was observed on the Polyflux® membrane, while significant growth was observed on the AN69 membrane (see FIG. 2).

Example 2

Circular specimens having a diameter of 44 mm of a) a copolymer of acrylonitrile and sodium methallylsufonate (AN69, Gambro) and b) a copolymer of acrylonitrile and sodium methallylsufonate, coated with polyethyleneimine (AN69ST, Gambro) were cut from sheet membranes, placed in 60 mm petri dishes and secured with aluminum rings having a diameter of 38 mm.

Figure 3:
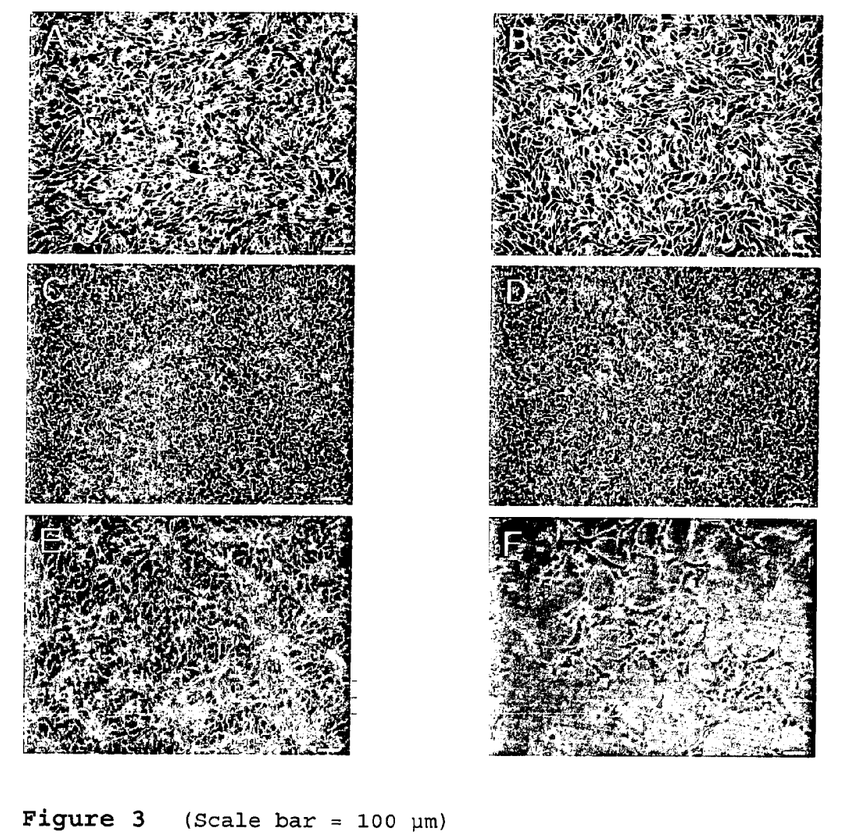
FIG. 3 shows LM micrographs of several human renal cell types cultured for 14 days on AN69 membranes:
A) human proximal tubule cells (hPTC) on AN69ST;
B) human distal tubule cells (hDTC) on AN69ST;
C) a mixture of human proximal tubule cells with other renal cells (hPneg) on AN69ST;
D) a mixture of human distal tubule cells with other renal cells (hDneg) on AN69ST;
E) human proximal tubule cells (PTC P5) on AN69ST;
F) human proximal tubule cells (PTC P5) on AN69.

Different fractions of primary human renal tubule cells cells were seeded over the whole area of the petri dishes and cultured using M199 medium+10% FCS. The results after 14 days of culturing are shown in FIG. 3:
- G) human proximal tubule cells (hPTC) on AN69ST;
- H) human distal tubule cells (hDTC) on AN69ST;
- I) a mixture of human proximal tubule cells with other renal cells (hPneg) on AN69ST;
- J) a mixture of human distal tubule cells with other renal cells (hDneg) on AN69ST;
- K) human proximal tubule cells (PTC P5) on AN69ST;
- L) human proximal tubule cells (PTC P5) on AN69.

As can be seen from the comparison of pictures E and F, primary human renal cells proliferate much better on AN69ST.

Example 3

Two different cell types:
- (a) a mixture of primary human proximal and distal tubule cells cells (hNF) of passage 2 (1/400 mm$^2$), and
- (b) commercially available human renal proximal tubule cells (RPTEC, Lonza/Clonetics) of passage 3 (1/200 mm$^2$)

were cultured on AN69ST membranes in different media:
- (i) M199 (Sigma)+10% FCS (comparative)
- (ii) Keratinocyte-SFM (Invitrogen)+20-30 µg/ml BPE+5 ng/ml EGF+1.2 mmol/l Ca$^{2+}$+1 vol.-% FCS (according to the present invention)

for seven days.

Figure 4:
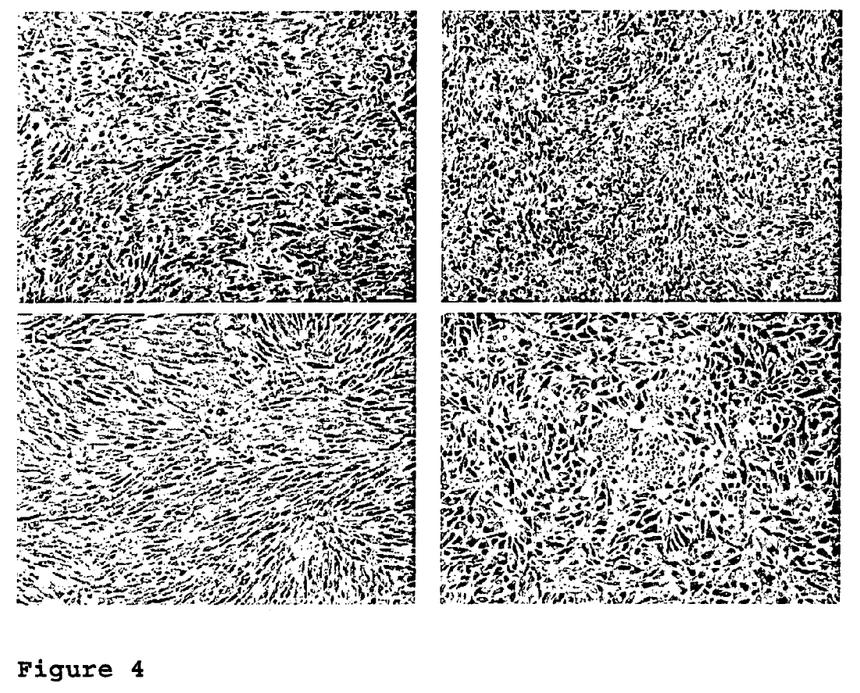
FIG. 4 shows LM micrographs of NF-P2 (A, B) and RPTEC-P3 (C, D) cells cultured for 7 days on AN69ST membranes in a standard medium (A, C) and the medium of the present invention (B, D).

The results are shown in FIG. 4:
- A) hNF-P2 in medium (i);
- B) hNF-P2 in medium (ii);
- C) RPTEC in medium (i);
- D) RPTEC in medium (ii).

Cells cultured in medium (i) show a fusiform morphology, while cells cultured in medium (ii) have developed the desired isodiametric morphologies.

After culturing the RPTEC cells on AN69ST for 30 days in the different media, a cell number of $8.8 \cdot 10^5$ cells and a cell density of 1956 cells/mm$^2$ were obtained with medium (ii), while only $4.9 \cdot 10^5$ cells and a cell density of 1088 cells/mm$^2$ could be obtained with medium (i).

Example 4

A hollow fiber module as shown in FIG. 1, comprising 64 hollow fibers made of a copolymer of acrylonitrile and sodium methallylsulfonate (Nephral®, Gambro), each fiber having an inner diameter of 210 µm, a length of 245 mm$^2$, corresponding to a total membrane area of ca. 10,300 mm$^2$, was used to culture HK-2 cells.

The external compartment (EC) of the module was washed three times with saline, then filled with saline and sealed. Subsequently, the internal compartment (IC) was flushed with saline. A suspension of cells in PBS having a concentration of 0.5-1.0 Mio cells/ml was prepared and slowly fed to the IC of the module through one of the inlets (4) while liquid was withdrawn from the EC through one of the outlets (5). After the total volume of the suspension had been fed to the module, the inlets/outlets (4) of the IC were sealed and perfusion of the culture medium through the EC was started. After 12 hours of perfusion, the IC was rinsed with culture medium for 10 minutes to remove non-adhered cells and then the inlets/outlets (4) of the IC were sealed again.

Figure 5:
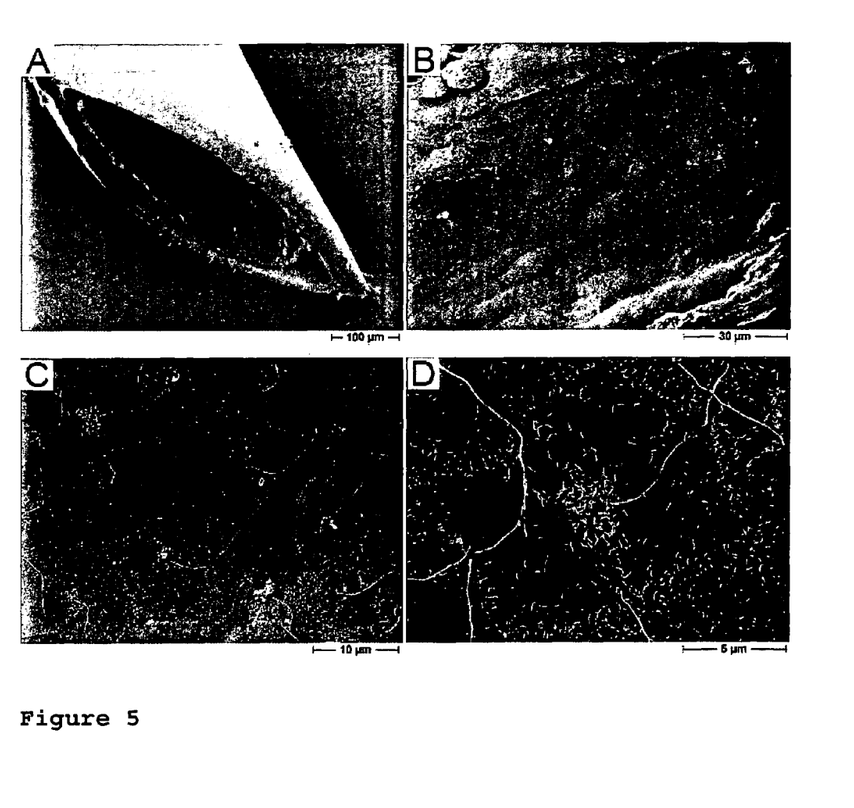
FIG. 5 shows REM pictures of HK-2 cells cultured for 57 days in Nephral® hollow fiber membranes.

The results after 57 days of perfusion are shown in FIG. 5. An epithelial cell layer has been formed and tight junctions and cilliae indicate morphological differentiation.

Example 5

A hollow fiber module as used in Example 4, but comprising 64 hollow fibers made of a copolymer of acrylonitrile and sodium methallylsulfonate and coated with polyethyleneimine (Nephral® ST, Gambro), was used to culture hDTC-P2 using medium (i) of Example 3 as culture medium, and hNF-P1 cells using medium (ii) of Example 3 as culture medium. The procedure described in Example 4 was used to culture and expand the cells.

Figure 6:
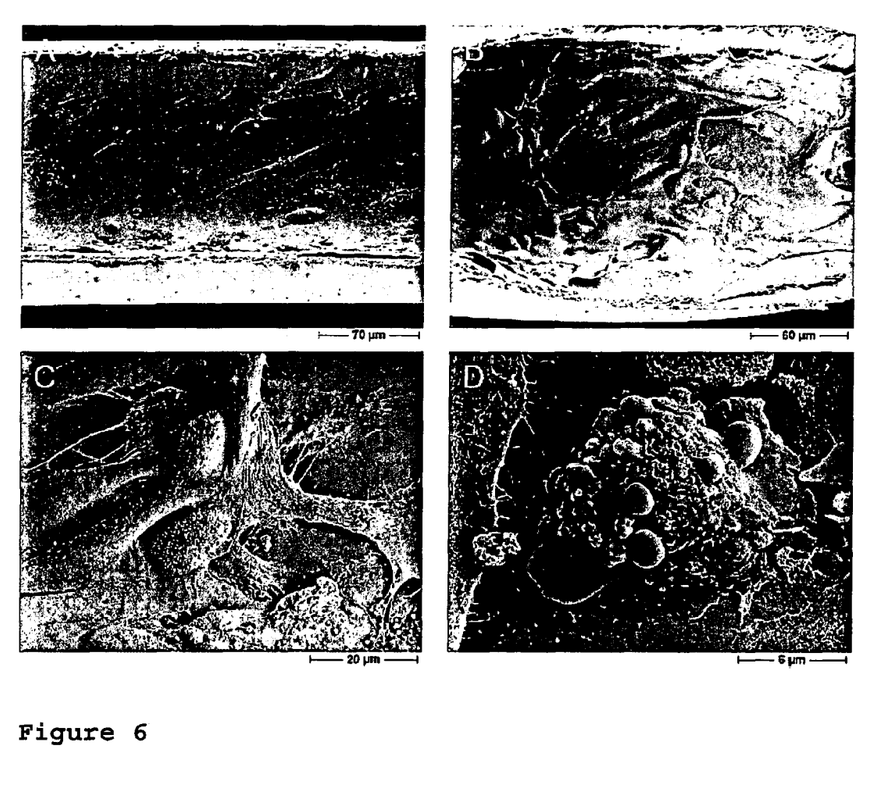
FIG. 6 shows REM pictures of hDTC-P2 cells cultured for 11 days in Nephral® ST hollow fiber membranes.

The results for hDTC-P2 after 11 days are shown in FIG. 6.

Figure 7:
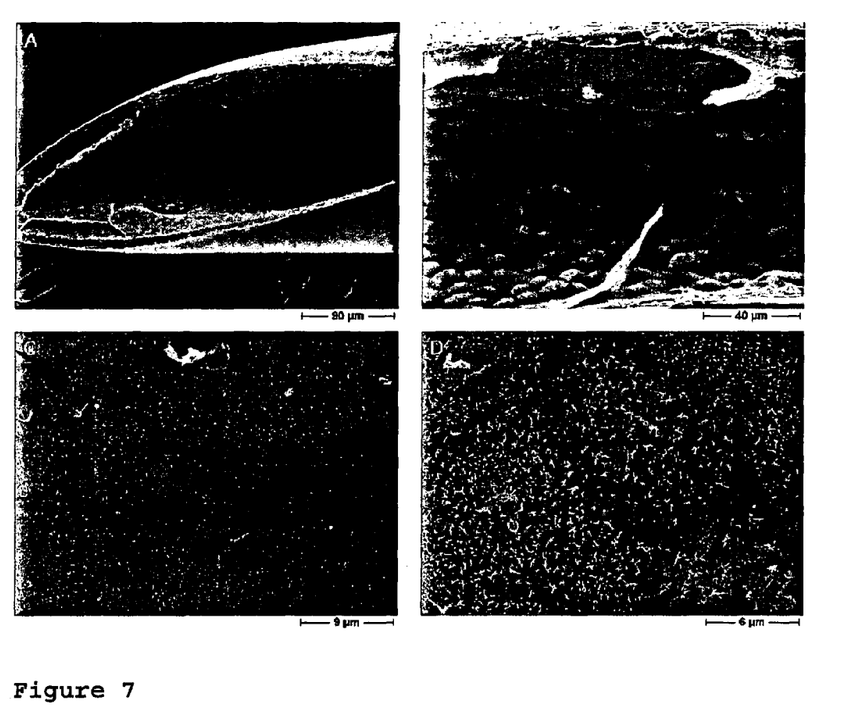
FIG. 7 shows REM pictures of hNF-P2 cells cultured for 14 days in Nephral® ST hollow fiber membranes.

The results for hNF-P2 after 14 days are shown in FIG. 7.

The invention claimed is:

1. A method of culturing adherent renal cells comprising providing a membrane comprising a copolymer of acrylonitrile and sodium methallylsulfonate, and further comprising polyethyleneimine, and heparin, and inoculating the membrane with adherent renal cells.

2. A method of culturing primary human renal tubule cells comprising providing a membrane comprising a copolymer of acrylonitrile and sodium methallylsulfonate, and polyethyleneimine, and heparin, and inoculating the membrane with primary human renal tubule cells.

3. A device for culturing, storing and expanding adherent renal cells, comprising a membrane comprising a copolymer of acrylonitrile and sodium methallylsulfonate and further comprising polyethyleneimine and heparin.

4. The device of claim 3, wherein the membrane is in the form of at least one sheet.

5. The device of claim 3, wherein the membrane is in the form of at least one hollow fiber.

6. The device of claim 3 further comprising two fluid compartments, wherein the membrane forms an interface between the two fluid compartments.

7. A process for expanding adherent renal cells comprising providing a membrane comprising a copolymer of acrylonitrile and sodium methallylsulfonate and further comprising polyethyleneimine, and heparin, and culturing the adherent renal cells on a surface of the membrane.

8. The process of claim 7, wherein providing a membrane comprising a copolymer of acrylonitrile and sodium methallylsulfonate and further comprising polyethyleneimine and heparin comprises providing a hollow fiber membrane comprising a copolymer of acrylonitrile and sodium methallylsulfonate and further comprising polyethyleneimine and heparin.

9. The process of claim 7 wherein the culturing comprises:
   a) seeding the membrane with adherent renal cells;
   b) propagating the adherent renal cells;
   c) detaching the adherent renal cells from the membrane; and
   d) collecting the detached adherent cells.

10. The process of claim 9, wherein b) propagating the adherent renal cells is terminated after a confluent layer of adherent renal cells has been formed on the membrane.

11. The process of claim 9 wherein a) seeding the membrane with adherent renal cells b) propagating the adherent renal cells, c) detaching the adherent renal cells from the membrane; and d) collecting the detached adherent cells are repeated using the same membrane.

12. An artificial kidney comprising a membrane comprising a copolymer of acrylonitrile and sodium methallylsulfonate, and further comprising polyethyleneimine, and heparin, and renal cells adhered to the surface of the membrane.

13. The device of claim 4 further comprising two fluid compartments, wherein the membrane forms an interface between the two fluid compartments.

14. The device of claim 5 further comprising two fluid compartments, wherein the membrane forms an interface between the two fluid compartments.

15. The process of claim 8 wherein the culturing comprises:
   a) seeding the membrane with adherent renal cells;
   b) propagating the adherent renal cells;
   c) detaching the adherent renal cells from the membrane ; and
   d) collecting the detached adherent cells.

16. The process of claim 15, wherein b) propagating the adherent renal cells is terminated after a confluent layer of adherent renal cells has been formed on the membrane.

17. The process of claim 10 wherein a) seeding the membrane with adherent renal cells b) propagating the adherent renal cells, c) detaching the adherent renal cells from the membrane; and d) collecting the detached adherent cells are repeated using the same membrane.

* * * * *